(12) United States Patent
Chevallet et al.

(10) Patent No.: US 6,579,494 B1
(45) Date of Patent: Jun. 17, 2003

(54) PROCESS AND DEVICE FOR STERILIZING AND DISPENSING A LIQUID FOR MEDICAL USE

(75) Inventors: Jacques Chevallet, Sérézin du Rhône (FR); Thierry Court, Villeurbanne (FR); Michael John Dunkley, Cambridge (GB); Alain Frugier, Tignieu (FR); Lennart Jonsson, Furulund (SE); Nicholas John Kerry, Burwell (GB); Hiram Rada, Lyons (FR); Jean-Louis Romarie, Décines Charpieu (FR)

(73) Assignee: Hospal Industrie, Meyzieu cedex (FR)

( * ) Notice: Subject to any disclaimer, the term of this patent is extended or adjusted under 35 U.S.C. 154(b) by 0 days.

(21) Appl. No.: 09/537,307

(22) Filed: Mar. 29, 2000

Related U.S. Application Data
(60) Provisional application No. 60/127,179, filed on Mar. 30, 1999.

(51) Int. Cl.[7] .............................................. G05B 23/00
(52) U.S. Cl. ........................... 422/3; 210/143; 210/149; 210/175; 422/1; 422/38; 422/41; 422/109; 422/116; 422/308
(58) Field of Search .......................... 422/1, 3, 38, 40, 422/41, 109, 105, 116, 307, 308; 210/143, 149, 175

(56) References Cited

U.S. PATENT DOCUMENTS

| | | |
|---|---|---|
| 4,534,986 A | 8/1985 | Hasting |
| 4,542,034 A | 9/1985 | Aule et al. |
| 4,834,888 A | 5/1989 | Polaschegg |
| 5,476,592 A | 12/1995 | Simard |

FOREIGN PATENT DOCUMENTS

| | | |
|---|---|---|
| DE | 40 25 570 A1 | 10/1991 |
| EP | 0 270 794 | 6/1988 |
| EP | 0 428 009 A1 | 5/1991 |
| EP | 0 462 606 A1 | 12/1991 |
| EP | 0 622 087 A1 | 11/1994 |
| GB | 2 034 584 A | 6/1980 |
| WO | WO 93/05667 | 4/1993 |
| WO | WO 96/05883 | 2/1996 |

*Primary Examiner*—Krisanne Thornton
(74) *Attorney, Agent, or Firm*—Finnegan, Henderson, Farabow, Garrett & Dunner, L.L.P.

(57) ABSTRACT

A device for preparing a sterile liquid includes structure for validating a sterilization treatment applied to the liquid. The validating structure includes structure for calculating, from at least one operating parameter of the device, a parameter representing a sterilizing value for the sterilization treatment, and structure for comparing the calculated parameter to a threshold value corresponding to the sterility of the liquid.

46 Claims, 3 Drawing Sheets

PROCESS AND DEVICE FOR STERILIZING AND DISPENSING A LIQUID FOR MEDICAL USE

This application relies on the benefit of priority of U.S. Provisional Patent Application Serial No. 60/127,179, filed Mar. 30, 1999.

The present invention relates to a process and a device for sterilizing and dispensing a liquid for medical use.

Many surgical and medical treatments exist which require the use of large amounts of sterile liquid, in particular of liquid to be injected into a body cavity or into the bloodstream.

For example, mention may be made of haemofiltration, which is one of the treatments used to overcome renal insufficiency. Haemofiltration consists in extracting, from the blood of a patient, by means of ultrafiltration, a determined amount of plasmatic water and in simultaneously infusing the patient with a smaller amount of a so-called substitution solution, which is sterile and contains the main electrolytes of the blood in respective concentrations which are identical or close to those of the blood of a healthy patient. For a four-hour haemofiltration session, it is not uncommon to prescribe an exchange volume for which about sixteen liters to twenty liters of substitution solution are required.

Another example of a treatment which requires the use of a large amount of sterile liquid is automatic peritoneal dialysis. The principle of peritoneal dialysis, the purpose of which is also to overcome renal insufficiency, is to infuse, into the peritoneal cavity of a patient, a determined amount of a sterile solution containing an osmotic agent such as glucose as well as the main electrolytes of the blood in respective concentrations similar to those of the blood of a healthy patient. The solution thus infused is left to stand in contact with the peritoneum, which behaves like a natural dialysis membrane, for the time required for the solution to become optimally enriched in blood impurities (urea, creatinine). The waste solution containing added plasmatic water which the glucose has caused to migrate into the peritoneal cavity is then drained from the patient's abdomen and is then replaced with fresh solution.

In the standard method of peritoneal dialysis, known as "continuous ambulatory peritoneal dialysis (CAPD)", it is the patient himself who carries out the operations of draining and filling his peritoneal cavity, by connecting a drain bag or a solution bag to the end of a catheter permanently installed through his abdominal wall. The transfer of liquid from the peritoneal cavity to the collecting bag and from the bag of solution to the peritoneal cavity takes places by gravity, the collecting bag being kept below the level of the abdomen and the bag filled with fresh solution being kept above the level of the abdomen. Typically, a patient carries out the draining-filling operations which have just been described four to five times a day and each exchange involves two liters of liquid.

In the peritoneal dialysis method known as "automatic peritoneal dialysis (APD)", the draining-filling operations are carried out overnight, while the patient is resting, using a machine essentially comprising a pump for circulating the drain liquid and the fresh dialysis solution, a heating device for heating the fresh solution, a balance for weighing the bags of fresh solution and of drain liquid and for measuring the weight loss, and a programmable control unit for controlling the alternation of the cycles of dwelling and of draining-filling. Since this mode of treatment is administered by a machine and while the patient is resting, it allows a larger number of exchanges than in standard peritoneal dialysis: five or ten exchanges are usually carried out per night, requiring from ten to thirty liters of fresh solution.

In general, the sterile liquids used for carrying out medical treatments of the type which have just been mentioned are prepared industrially and are packaged in flexible plastic bags. Besides the fact that it is unsuitable for the production of unstable solutions (sodium bicarbonate), this preparations method has several drawbacks, in particular the cost of transporting and storing heavy and bulky bags of solutions and the need to manage products which have expiry dates. To overcome these drawbacks, devices have been proposed for preparing sterile medical liquids at the place of use.

Document EP 0,662,087 describes a process for the on-line preparation of a sterile, pyrogen free liquid which is obtained by filtering a dialysis liquid produced by a standard dialysis machine.

Document GB 2,034,584 describes a process for preparing a sterile liquid whose sterility is obtained by heating the liquid to a determined sterilization temperature for a determined time. A device for carrying out this process, which is designed to fill bags with the sterile liquid, comprises:

heating means for raising the temperature of a liquid immediately upstream of a sterilization unit consisting of a portion of heat-insulated circuit;

a circuit connected to the sterilization unit, which has a first end connected to a source of liquid to be sterilized and a second end connected to a connector which has a first outlet for delivering a sterile liquid;

a discharge pipe connected to a second outlet of the connector, and pumping means for circulating the liquid in the main circuit.

This device also comprises means for degassing by heating the liquid to be sterilized upstream of the heating means and of the sterilization unit in order to avoid the entrainment of bubbles by the liquid during the sterilization treatment.

Although that document presents the prior degassing as a satisfactory solution to the problem posed by the presence of bubbles in a liquid subjected to a sterilization treatment, it is doubted that, without other precautions, a liquid brought to a high temperature would not entrain bubbles simply because it has been degassed before hand.

Moreover, that document avoids two questions which, according to the invention, need to be answered when the sterilization of a liquid is undertaken. The first question relates to what is meant by the term "sterilization" and the second question relates to the microbiological quality of the device used to carry out the sterilization.

It should be recalled that the term "sterility" defines a microbiological quality of the object said to be "sterile" and that, according to standard EN 556 and also according to the US and European Pharmacopoeias, in order for a device or a liquid to be labeled as sterile, it is necessary for the theoretical probability of the presence of a viable microorganism in this device or this liquid to be less than or equal to $10^{-6}$.

However, checking this $10^{-6}$ level of presence by examining the finished product is impossible on two counts, both because the sampling required for this check according to the Poisson probability distribution is unachievable, and because, in practical terms, the manipulations required to check the samples entail a probability of contamination which is such that, even if the sampling could be achieved, the results of the check would be erroneous.

One aim of the invention is to produce a sterilization process and a device for carrying out this process which ensure the sterility of the liquid prepared by the device according to the process.

In order to achieve this aim, a device is provided, in accordance with the invention, comprising:

main adjustable heating means for raising the temperature of a liquid inside a heating chamber, a main circuit comprising:
  a first pipe, one end of which can be connected to a source of liquid to be sterilized, and another end of which is connected to an inlet of the heating chamber, and
  a second pipe, one end of which is connected to an outlet of the heating chamber, and another end of which is connected to a connector which has a first outlet for delivering a sterile liquid, first pumping means for circulating the liquid in the main circuit, characterized in that it comprises:
  means for validating a sterilization treatment applied to the liquid, comprising calculation means for calculating a parameter representing the sterilizing value (F0) for the treatment from the value for at least one operating parameter of the device (Q, Tin, THin, Tout, THout), and comparison means for comparing the calculated value of the parameter representing the sterilizing value (F0) to a first threshold value F0min1 corresponding to the sterility of the liquid.

For example, the calculation means are provided to calculate the parameter representing the sterilizing value (F0) for the treatment applied to the liquid from a mathematical model of the temperature distribution in the heating chamber, the temperature (Tin, Tout) of the liquid entering or leaving the heating chamber, the temperature of the heating liquid (THin) and the flow rate of the liquid (Q) in the heating chamber.

According to one characteristic of the invention, the device also comprises control means for controlling the pumping means and/or the heating means such that the calculated value of the parameter representing the sterilizing value (F0) is greater than the first threshold value F0min1.

According to another characteristic of the invention, the device also comprises means for preventing the formation of bubbles in the liquid during the sterilization of the liquid, these means comprising first means, such as a valve with adjustable opening, for adjusting the pressure of the liquid to a pressure value above the vaporization pressure of the liquid, irrespective of the temperature of the liquid, the first means for adjusting the liquid pressure being provided on the second pipe of the main circuit.

According to yet another characteristic of the invention, the device also comprises means for sterilizing the second pipe and the connector comprising:
  means for validating a sterilization treatment applied to the second pipe and to the connector, and
  means for preventing the formation of bubbles in the liquid during the sterilization of the second pipe and of the connector.

A subject of the invention is also a process consisting in:
  heating the liquid in a heating chamber to a temperature and for a period which are suitable for sterilizing the liquid;
  validating the sterilization treatment applied to the liquid by calculating a parameter representing the sterilizing value (F0) for the treatment from the value of at least one operating parameter for the device (Q, Tin, THin, Tout, THout), and by comparing the calculated value of the parameter representing the sterilizing value (F0) to a first threshold value F0min1 corresponding to the sterility of the liquid.

Other characteristics and advantages of the invention will become apparent on reading the description which follows. Reference will be made to the attached drawings, in which.

Figure 1:
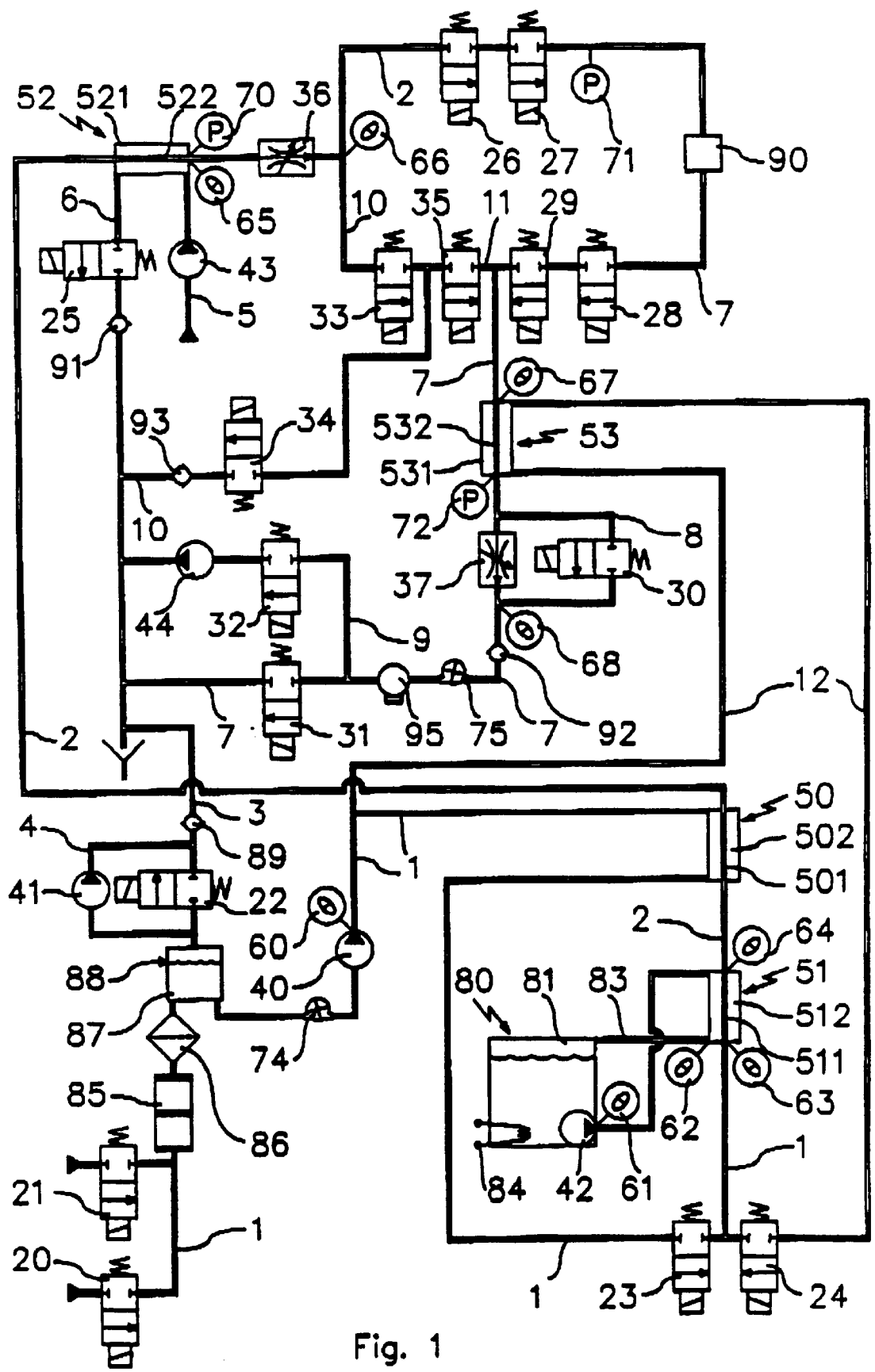
FIG. 1 represents the scheme of a first embodiment of a device according to the invention.

The device for preparing and dispensing a sterile liquid, represented in FIG. 1, essentially comprises main heating means 80 with a heating chamber 511 for the liquid, and a main circuit with a first pipe 1 connected to an inlet of the heating chamber 511 and a second pipe 2 connected to an outlet of the heating chamber 511.

The main heating means 80 comprise a reservoir 81 for a heating liquid (for example oil or ethylene glycol) connected via a heating liquid recirculation pipe 83 to a tubular sleeve 512 which surrounds the chamber 511 for heating the liquid to be sterilized. The heating chamber 511 and the sleeve 512 form a first heat exchanger 51. The main heating means 80 also comprise an adjustable heating member 84 for heating the heating liquid, as well as a pump 42 for permanently circulating the heating liquid in the exchanger 51.

The first pipe 1 has two inlets respectively controlled by means of two valves 20, 21: a first inlet is connected to a water source (valve 20) and the second inlet is connected to a source of medical liquid (valve 21). The following members are provided in the first pipe 1, in order, starting from the valves 20, 21: a conductivity meter 85 for measuring the conductivity of the liquid in the circuit and for checking whether the liquid is water or a solution; a filter 86; a degassing chamber 87 fitted with a level detector 88; a flow meter 74; a first pump 40; first additional heating means 501 and a valve 23. A purge pipe 3, which is fitted with a valve 22 and a non-return valve 89, connects a high point of the degassing chamber 87 to the drain. A branch pipe 4 fitted with a pump 41 is connected to the purge pipe 3 so as to short-circuit the valve 22. During functioning, each time the level detector 88 detects no more liquid, then either the valve 22 is opened for a determined period if the pressure of the liquid in the circuit upstream of the first pump 40 is above atmospheric pressure, or the pump 41 is switched on for a determined period, if the pressure of the liquid in the circuit upstream of the pump 40 is below atmospheric pressure.

The second pipe 2 connects the outlet of the heating chamber 511 to an outlet of the main circuit, which consists of a special sterilizable connector 90, with one inlet and two outlets. A connector of this type is described, for example, in patent No WO 96/05883. The following members are provided on the second pipe 2, in order, starting from the exchanger 51: first additional cooling means 502, which are advantageously combined with the first additional heating means 501 to form a second heat exchanger 50; main cooling means comprising a tubular sleeve 521 surrounding the pipe 2 over a part 522 of its length to form a third heat exchanger 52, the sleeve 521 having an inlet connected to a cold water source via a feed pipe 5 on which is provided a pump 43, and an outlet connected to the drain via a discharge pipe 6 on which are provided, in order, starting from the exchanger 52: a valve 25 and a non-return valve 91; a first means of liquid pressure adjustment consisting of a valve 36 with adjustable opening; two valves 26, 27 which are in duplicate for safety reasons; and the sterilizable connector 90, which has an inlet connected to the end of the pipe 2, a first outlet (not shown) for connecting the device to a container or to a patient and a second outlet connected to one end of a first discharge pipe 7, the other end of which is connected to the drain.

As will be explained later in detail, the first discharge pipe 7 is used during the sterilization of the second pipe 2 and of the connector 2, and during the drainage of a patient's peritoneal cavity, when the device according to the invention is used for treating a patient by peritoneal dialysis. The following members are provided on the first discharge pipe 7, in order, starting from the connector 90: two valves 28, 29 which are in duplicate for safety reasons; a second additional cooling means 531; a second means of liquid pressure adjustment consisting of a valve 37 with adjustable opening, which can be by-passed by means of a branch pipe 8, fitted with a valve 30; a non-return valve 92; a second flow meter 75; a blood detector 95; a valve 31. A branch pipe 9 fitted with a valve 32 and a second pump 44 is connected to the discharge pipe 7 so as to short-circuit the valve 31. As will be explained later in detail, the second pump 44 is used for draining the patient's peritoneal cavity. This second pump can also be used at the start of a step of filling a container or the peritoneal cavity of a patient subjected to a peritoneal dialysis treatment.

A second discharge pipe 10 has one end connected to the second pipe 2 of the main circuit, immediately downstream of the adjustable valve 36, and its other end is connected to the drain. This pipe 10 is provided, in order, starting from the second pipe 2, with a first valve 33, a second valve 34 and a non-return valve 93. As is described in detail later, this discharge pipe 10 is used during a peritoneal dialysis treatment, outside of the steps for filling the patient's peritoneal cavity.

The first and the second discharge pipes 7, 10 are connected via a connecting pipe 11, one end of which is connected to the pipe 7, between the valve 29 and the second additional cooling means 531, and the other end of which is connected to the pipe 10, between the valves 33 and 34. A valve 35 is provided on this connecting pipe 11.

The device for preparing and dispensing a sterile liquid according to the invention also comprises a third pipe 12 mounted in parallel to the first pipe 1, between a first point located downstream of the first pump 40 and a second point located upstream of the first exchanger 51. This third pipe 12 is provided, in order, starting from the pump 40, with a second additional heating means 532 and a valve 24. Advantageously, the second additional heating means 532 is combined with the second additional cooling means 531 to form a fourth heat exchanger 53.

In accordance with the invention, the third pipe 12 and its accessories, along with the adjustable valve 37 provided on the first discharge pipe 7, form a part of means for sterilizing the device (second pipe 2 and connector 90).

The device represented in FIG. 1 also includes a plurality of pressure and temperature measuring means provided at various points on the main circuit (pipes 1 and 2), on the first discharge pipe 7 and on the main heating means 80. In particular, a pressure sensor is connected to the following pipes, at the following points:

on the second pipe 2, between the third exchanger 52 and the first adjustable valve 36 (reference number 70);

on the second pipe 2, immediately upstream of the connector 90 (reference number 71);

on the first discharge pipe 7, between the fourth exchanger 53 and the second adjustable valve 37 (reference number 72).

A temperature sensor is connected to the following pipes, at the following points:

on the first pipe 1, immediately downstream of the first pump 40 (reference number 60);

at the inlet and at the outlet of the heating chamber 511 of the main heating means 80 (reference numbers 63, 64);

on the pipe 83 for recirculating the heating liquid, at the outlet of the reservoir 81 (reference number 61) and at the outlet of the sleeve 512 (reference number 62);

on the second pipe 2, between the third exchanger 52 and the first adjustable valve 36 (reference number 65);

on the second pipe 2, at the junction between this pipe and the second discharge pipe 10 (reference number 66);

on the first discharge pipe 7, at the inlet of the fourth exchanger 53 (reference number 67);

on the first discharge pipe 7, downstream of the second adjustable valve 37 (reference number 68).

Manufacturers of suitable components for the device of FIG. 1, as well as the reference of such components are indicated in the following table.

| COMPONENT | FIG. 1 REFERENCE N° | MANUFACTURER | MANUFACTURER REFERENCE |
| --- | --- | --- | --- |
| Blood leak detector | 95 | HOSPAL DASCO | 6957989 |
| Degassing chamber | 87 | HOSPAL DASCO | 6965925 |
| Conductivity meter | 85 | HOSPAL DASCO | 6945109 6962195 |
| Gear pump | 43 | HYDROFLUID | prototype HOSPAL RD |
| Peristaltic pump | 41 | ASF | 6959100 |
| Gear pump | 40, 44 | THUTILL | B9049PYWQS |
| Filter | 86 | HOSPAL DASCO | 6958821 |
| Flow meter | 74, 75 | HOSPAL DASCO | 6955959 |
| Heat exchanger | 50, 51, 52, 53 | PARKER FLUID CONNECTOR | type DHTC SS4 |
| Level detector | 88 | HOSPAL DASCO | 6957054 |
| Main heating means | 42, 80, 81, 84 | BIOBLOCK | type HUBERT (G85111) |

-continued

| COMPONENT | FIG. 1 REFERENCE N° | MANUFACTURER | MANUFACTURER REFERENCE |
|---|---|---|---|
| Recirculation pipe | 83 | PROLABO | 06521000 |
| Non-return valve | 89, 91, 92, 93 | HOSPAL DASCO | 6950737 |
| Sterilizable connector | 90 | CAMBRIDGE CONSULTANTS | prototype |
| Valve with adjustable opening | 36, 37 | NUPRO (SWAGELOK) | type RL3 (SS-3K-RL3-VI |
| Pressure sensor | 70, 71, 72 | KELLER | PA-10-8838 |
| Solenoid valve | 20, 21, 22, 25, 31, 32 | SIRAI | D111S15Z612A |
| Solenoid valve | 23, 24, 26, 27, 28, 29, 30, 33, 34, 35 | BURKERT | type 255 (35003999) |
| Stainless pipe | 1, 2, 3, 4, 5, 6, 7, 8, 9, 10, 11, 12 | FAURE AUTOMATISME | 36403031 |
| Temperature sensor | 60, 61, 62, 63, 64, 65, 66, 67, 68 | FAURE AUTOMATISME | TC2EJ20M3AJR1 |

The device according to the invention also includes a control unit (not shown). This unit receives the date measured by the pressure sensors 70 to 72, by the temperature sensors 60 to 68 and by the flow meters 74 and 75. From these data, from the set value for the operating parameters communicated by an operator (in particular, optionally, the flow rate of the liquid) and from a control and checking program stored in a memory of the control unit, this unit controls and checks the functioning of the device. In particular, in accordance with the invention, the control unit checks and validates the sterilization treatment applied to the liquid, on the one hand, and to the device, on the other hand.

In accordance with the invention, in order to ensure that the liquid leaving the main heating means 80 is sterile at all times, it is first necessary to define a parameter representing the sterilizing value for the treatment carried out, which can be calculated, for example, from an algorithm modeling the temperature distribution inside the exchanger 51 for the main heating means 80, and from the value of at least one of the parameters liable to influence the sterilization treatment, namely the flow rate Q of the liquid to be sterilized in the exchanger 51, the temperature (Tin) of the liquid to be sterilized entering the exchanger 51 and the temperature (THin) of the heating liquid entering the exchanger 51. Since the temperature at the outlet of the exchanger 51 (temperature of the sterilized liquid and temperature of the heating liquid) are linked to the temperatures at the inlet of the exchange 51, it also possible to take into account in the calculations the temperature (Tout) of the sterilized liquid leaving the exchanger 51 and/or the temperature (THout) of the heating liquid leaving the exchanger 51.

When the parameter representing the sterilizing value for the treatment is defined, a set value for this parameter is then chosen which is both high enough to correspond to an effective sterilization of the liquid, and as low as possible in order to prevent or limit the degradation of the liquid to be sterilized when this liquid is heat-sensitive (as in the case of solutions for peritoneal dialysis which contain glucose).

During functioning, the control unit is programmed to calculate, at regular intervals, the value of the parameter representing the sterilizing value for the treatment, from the algorithm of temperature distribution in the exchanger 51, and the temperature and flow rate data measured by the corresponding sensors. Each time that a new value for the parameter is calculated, the control unit checks that this calculated value is higher than the set value and it validates the sterilization of liquid.

This checking process, which allows validation of the effective sterilization of the liquid as resulting from the correct use of the device according to the invention, can be passive. The reason for this is that, given that the sterile state is a crucial characteristic of a medical liquid which needs to be injected, it is possible to envisage a standard operating mode for the sterilization device in which the choice of the flow rate for the liquid to be sterilized is limited to a restricted number of different predetermined values (for example three) and in which all of the other operating parameters for the device are preset as a function of the predetermined flow rates, such that the functioning of the device is simplified as much as possible. In this case, the checking process described above is used merely to validate the sterilization.

Naturally, it is also possible to envisage an operating mode for the device in which the choice of flow rate of liquid to be sterilized is free within a range of determined values. In this case, the control unit can be used to calculate, from the chosen flow rate and from the set value for the parameter representing the sterilizing value, the other operating parameters for the device, in particular the temperature of the heating liquid. During functioning, the control unit regularly adjusts the flow rate of the first pump 40 and/or the temperature of the heating liquid, such that the calculated value of the parameter is always greater than the set value.

In one embodiment of the invention, the parameter denoted in the literature as F0 (expressed in minutes) is used as parameter representing the sterilizing value for the sterilization process. It is recalled that F0 is the sum $F_T^Z$ of the cumulative sterilizing effects during a sterilization treatment (this sum being called "sterilizing value $F_T^Z$") when the reference temperature T is equal to 250° F. (121.1° C.) and the thermal inactivation value Z is equal to 18° F. (10° C.). As a reminder, the thermal inactivation value Z is the temperature increase which multiplies by ten the rate of destruction of a specific microorganism. Z=10° C. corresponds to a theoretical microorganism which is slightly more resistant than the microorganism reputed to be more heat-resistant than any other spore-forming microorganisms, *Bacillus stearothermophilus*. The canonical formula of F0 is as follows:

$$F0 = \int_0^t 10^{[\frac{T-121}{10}]} dt$$

This formula cannot be applied directly to the checking of a sterilization treatment in which the liquid to be sterilized is permanently flowing and in which the heating means used to raise the temperature of the liquid to be sterilized do not bring this liquid to the same temperature at all points in the heating chamber.

In accordance with the invention, when the heating means are arranged to heat the liquid to be sterilized along a portion of the pipe in which the liquid is circulating, the following formula can be used to calculate F0:

$$F0 = \int_0^L \frac{S}{Q} \times 10^{[\frac{T(y)-121}{10}]} dy$$

in which

L=length of the portion of pipe (heating chamber 511) via which the liquid to be sterilized is heated by the heating means 80;

S=internal cross section of the heating chamber 511;

Q=flow rate of the liquid to be sterilized in the heating chamber 511;

T(y)=equation of the temperature distribution of the liquid as a function of the distance from the inlet of the heating chamber 511.

Figure 3:
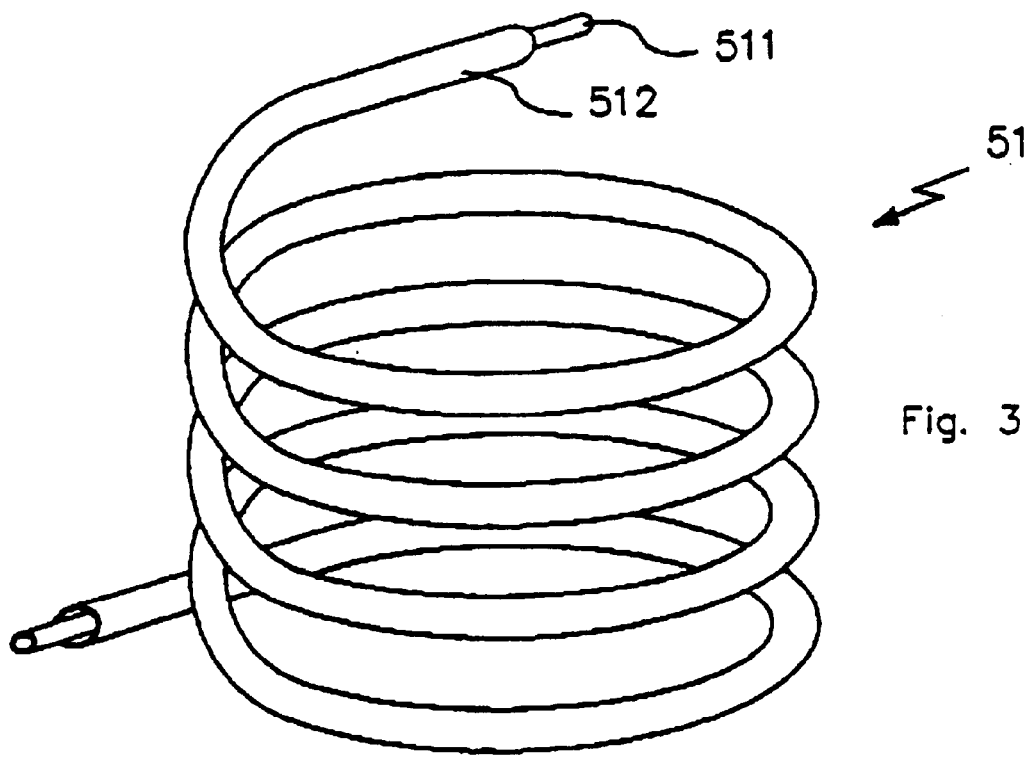
FIG. 3 is a view in perspective of a first embodiment of a heat exchanger according to the invention.

The equation T(y) depends on the structure of the exchanger 51 for the main heating means 80 and on its operating mode. For example, reference will be made to FIG. 3 which represents a first embodiment of an exchanger which is adapted to the device of the invention. This exchanger consists of two concentric pipes, the outer pipe forming a sleeve 512 around the inner pipe, which constitutes the heating chamber 511 mentioned above.

During functioning, the liquid to be sterilized and the heating liquid (ethylene glycol) from the reservoir 81 are circulated in counter-flow, in the inner pipe (heating chamber 511) and in the outer pipe (sleeve 512). The inside diameter of the heating chamber 511 is chosen such that, in the range of flow rates which includes the flow rates for operating the sterilization device (for example, 100 to 400 ml/min.), the flow of the liquid to be sterilized is always turbulent.

For an exchanger with an inner pipe made of stainless steel and an outer pipe made of copper and having the following dimensions:

| | |
|---|---|
| Length (cm) | 222 |
| Inner pipe volume (ml) | 26 |
| Outer pipe volume (ml) | 105 |
| Cross section of the inner pipe (cm²) | 0.117 |
| Area of the annular space between the inner and outer pipes (cm²) | 0.502 |
| Internal perimeter of the inner pipe (cm) | 1.213 |
| External perimeter of the inner pipe (cm) | 1.995 |
| Internal exchange area of the inner pipe (cm²) | 269 |
| External exchange area of the inner pipe (cm²) | 443 | the equation T(x) can be written in the following way:

$$T(y) = Tin + (THin - Tin) \times \frac{r \times [e^{-ny} - e^{-nL}]}{1 - r \times e^{-nL}}$$

in which:

Tin=temperature of the liquid to be sterilized entering the heating chamber 511 (such as measured by the sensor 63).

THin=temperature of the heating liquid entering the sleeve 512 (such as measured by the sensor 61).

$$r = 6 \times 10^{-5} \times Q^2 - 0,0577Q + 19,084$$

$$n = -\frac{1}{L} \ln\left[\frac{301415 - 958,18Q + Q^2}{292,6 + 65,72Q - 0,200453Q^3 + 0,00020948}\right]$$

Q=flow rate of the liquid in the heating chamber 511.

As emerges from this example, it is possible to calculate the sterilizing value F0 at any moment, from a measurement of the temperature Tin of the liquid to be sterilized entering the exchanger 51, a measurement of the temperature THin of the heating liquid entering the exchanger 51, a measurement of the flow rate Q of liquid to be sterilized and an equation modeling the temperature distribution inside the exchanger 51.

Throughout all the operating phases of the device according to the invention in which the device is programmed to produce a sterile liquid (water or medical liquid), the control unit validates the sterilization treatment carried out by checking that the calculated sterilizing value F0 is always greater than a first threshold value F0min1 corresponding to the sterility of the liquid.

In accordance with the invention, during a preliminary phase of operating the device, the main circuit of the device has to be sterilized, from the exchanger 51 up to and including the connector 90, i.e. beyond the connector 90, for example up to the level of the temperature sensor 67 connected to the first sterilization pipe 7. The sterilization of the main circuit can be considered as effective when all of the points in the main circuit downstream of the exchanger 51 have been brought, by means of the sterile liquid, to a minimum temperature T2 for a minimum period t2, which corresponds to a second set sterilizing value F0min2, such that:

$$F0\min2 = t2 \times 10^{[\frac{T2-121}{10}]}$$

Validation of the sterilization of the main circuit can be made simply by the control unit by checking that, during an uninterrupted interval at least equal to t2, the temperature of the liquid measured by the temperature sensor 67 has constantly been above T2.

Since the sterilization of the device is to be carried out with sterile water, during the initial phase of sterilizing the device, the control unit must validate both the sterilization of the liquid and sterilization of the main circuit. In other words, the control unit must check both that the sterilizing value for the sterilization treatment applied to the liquid is greater than F0min1 and that the sterilizing value for the sterilization treatment applied to the circuit is greater than F0min2.

When the device is used to administer an automated peritoneal dialysis treatment, the functioning of the device essentially comprises the following four phases:

The first phase corresponds to the initial sterilization of the device.

The second phase corresponds to a standby state in which the device is kept sterile and produces sterile water at a low flow rate. This second phase comes immediately after the initial sterilization of the device or between two active phases of functioning of the device, the filling of the patient's peritoneal cavity and the draining of this cavity after the liquid has dwelled therein for a determined period.

The third phase corresponds to the continuous production of the sterile solution for filling the patient's peritoneal cavity.

The fourth phase corresponds to the draining of the patient's peritoneal cavity while the device is kept sterile and produces sterile water at a low flow rate.

First phase: initial sterilization of the circuit.

In order to economize the liquid for medical use, the circuit is preferably sterilized with water (valve 20 open, valve 21 closed). During this first phase, which includes several steps, valve 23 is closed and valve 24 is open, such that the water made to circulate by the first pump 40 circulates in the third pipe 12. Moreover, the first adjustable valve 36 is fully open and the second adjustable valve 37 is only partially open, such that pressure in the circuit upstream of the valve is always greater than the pressure at which the water would begin to boil (if the water began to boil, it would not be possible to validate the sterilization of the circuit, since it would not be possible to certify that every point of the circuit has come into contact with water at a minimum temperature for a minimum uninterrupted period of time). The pumps 43 and 44 are not switched on.

In a first step of this first phase, the valves 26, 27, 28, 29, 30, 32, 34 are closed and the valves 33, 35, 31 are open, such that, downstream of the first adjustable valve 36, the water flows into a part of the second discharge pipe 10, into the connecting pipe 11 and then into the first discharge pipe 7.

In a second step of this first phase, the valves 26, 27, 28, 29 are open, such that the water then also flows into the end of the second pipe 2, through the connector 90, and then into the first discharge pipe 7, from its connection to the connector 90.

In a third step of the first phase, the valves 33, 35 are then closed, such that the water no longer circulates in the start of the second discharge pipe 10.

The duration of these three steps, as well as the flow rate of the water in the circuit, the degree of opening of the valve 37 and the intensity of the heating supplied by the main heating means 80 are either adjusted to preprogrammed values or are adjusted as a function of each other such that the sterilizing value for the sterilization treatment applied to the water and to the circuit is greater than the first and the second set value F0min1, F0min2. The control unit also checks that, given the actual operating conditions of the device, as measured by the various sensors, the effective sterilizing value is greater than F0min1 and than F0min2.

For example, during this first phase, the flow rate of water made to circulate by the pump 40 is adjusted to 250 ml/min., the pressure in the circuit upstream of the valve 37 is adjusted to seven bar and the temperature of ethylene glycol entering the exchanger 51 is adjusted to 165° C. (the pressure referred to throughout this document is the absolute pressure). The temperature of the water leaving the exchanger 51 is then at least equal to 153° C. and the temperature upstream of the fourth exchanger 53, as measured by the sensor 67, is at least equal to 131° C. The duration of the various steps is chosen such that the sterilizing value of the sterilization treatment applied to the liquid is greater than 30 min. and the sterilizing value of the sterilization treatment applied to the circuit is greater than 30 min.

Second phase: placing the device on standby.

The main aim of this phase is to provide sterile water at a temperature of 37° C. and at atmospheric pressure at the connector 90.

In a first step of this second phase, the valve 23 is open, such that the water made to circulate by the pump 40 flows both into the first pipe 1 and into the third pipe 12.

In a second step, the valve 24 is closed, such that the third pipe 12 is isolated. Moreover, the valve 25 for the main cooling means is open and the pump 43 is switched on. During this step, the water is cooled in the exchanger 52, which it leaves at about 37° C., while the first adjustable valve 36 is gradually closed and the second adjustable valve 37 is gradually opened, such that the water does not begin to boil at any time, irrespective of its temperature, and such that, when the adjustment of the valves 36, 37 is complete, the pressure upstream of the first adjustable valve 36 is about seven bar and the pressure upstream of the second adjustable valve 37 is about one bar (atmospheric pressure). The valve 30 mounted in parallel to the second adjustable valve 37 is closed.

In a third step, the valves 33, 34 are open, such that the water also flows in the second discharge pipe 10.

Lastly, in a fourth step, the valves 26, 27, 28, 29 are closed, such that the sterile water only flows in the second discharge pipe 10 and such that the water stands in the portion of circuit containing the connector 90. In this mode of operating the device, which is a standby mode, all of the sterile water is sent to the drain. For reasons of economy, the flow rate of the pump 40 is reduced to the minimum, i.e. down to a value (100 ml/min.) at which the flow of water in the heating chamber 511 remains turbulent. Preferably, the 80 is lowered accordingly. During this second phase, as in the phases which follow, the control unit checks at regular intervals that the sterilizing value F0 for the treatment applied to the water, as calculated from the measured values of the flow rate Q and of the temperatures (Tin, THin) at the exchanger 51 inlet, is always within a range of values which has the first set value F0min1 as a lower limit (for example between 30 min. and 40 min.).

Third phase: production of sterile medical liquid.

The aim of this third phase is to produce a sterile medical liquid and to infuse this liquid into the patient's peritoneal cavity. A first step consists in closing the valve 20 and opening the valve 21 which gives access to a source of medical liquid to be sterilized, such that the medical liquid replaces the water in the first pipe 1, in the second pipe 2 up to the first adjustable valve 36, and in the second discharge pipe 10.

The second step of the third phase consists in opening the valves 26, 27, 28, 29, 31 such that the sterile medical liquid replaces the water in the end of the second pipe 2, in the connector 90 and in the first discharge pipe 7. Next, the valves 33, 34 are closed, such that the liquid is now sent to the drain only via the first discharge pipe 7.

The third step consists in connecting the patient to be treated to the device by means of a flexible tube (not shown), one end of which is connected to the patient's catheter and another end of which is connected to the connector 90 of the device. During the preceding three steps, the flow rate of the medical liquid controlled by the pump 40 is adjusted to a set infusion flow rate suited to the patient. After the patient has been connected to the device, the flow rate of the liquid leaving the connector 90 (infusion flow rate) is process-linked to the comparison between the pressure measured by the pressure sensor 71 and a set pressure corresponding to a pressure which is acceptable for the patient. In order to vary the infusion flow rate, a first possibility consists in modifying the flow rate of the first pump 40, which may make it necessary to correspondingly modify the temperature of the heating liquid. In order not to have to vary the sterilization parameters (flow rate of the liquid, temperature of the heating liquid), another possibility consists in opening the valves 28, 29, 32, in closing the valve 31 and in setting the second pump 44 at the appropriate flow rate.

According to one variant of the invention, the filling of the patient's peritoneal cavity is not carried out at constant flow rate as soon as the patient is connected to the device, and the infusion at the nominal flow rate is preceded by a transient phase in which the flow rate is gradually increased until the nominal flow rate is reached. In order to be able to vary the infusion flow rate without having to modify the flow rate of the first pump 40 (i.e. the liquid sterilization parameters also), the first discharge pipe 7 and the second pump 44 are used to take a decreasing fraction of the liquid sterilized by the device from the connector 90 and to send it to the drain. To do this, before the patient is connected to the device, the valves 28, 29, 30, 32 are open, the valve 31 is closed and the second pump 44 is switched on at the same flow rate as the main pump 40. When the patient is connected to the device, the second pump 44 is controlled such that its flow rate decreases gradually until it becomes zero (pump 44 stopped).

This filling phase is complete either when a predetermined amount of liquid, calculated by means of the data supplied by the flow meters 74 and 75, has been infused, or when the pressure measured by the pressure sensor 71 reaches a predetermined pressure. In the latter case, the control unit calculates the total amount of liquid infused, by means of the data supplied by the flow meters 74, 75.

Fourth phase: draining the patient's peritoneal cavity.

This phase follows the standby phase described above, during which the device produces sterile water at a low flow rate in order to maintain the sterility of the device, this sterile water being sent to the drain via the second discharge pipe 10. In therapeutic terms, the draining of the patient's peritoneal cavity is ordered when the liquid infused during the previous filling phase has dwelled in the peritoneal cavity for a predetermined period.

Compared with the standby phase, the valves 28, 29, 30, 32 are open and the pump 44 is switched on at a predetermined flow rate. The pump 44 is stopped when the amount of liquid drained is equal to the amount of liquid previously infused, increased by an amount of liquid corresponding to the weight which the patient should lose during each dwelling phase. In an alternative embodiment, the pump 44 is stopped when the pressure measured by the pressure sensor 71 reaches a determined low threshold.

At the end of this draining phase, the valve 20 is closed and the valve 21 is opened, such that the device again sterilizes the medical liquid.

Figure 2:
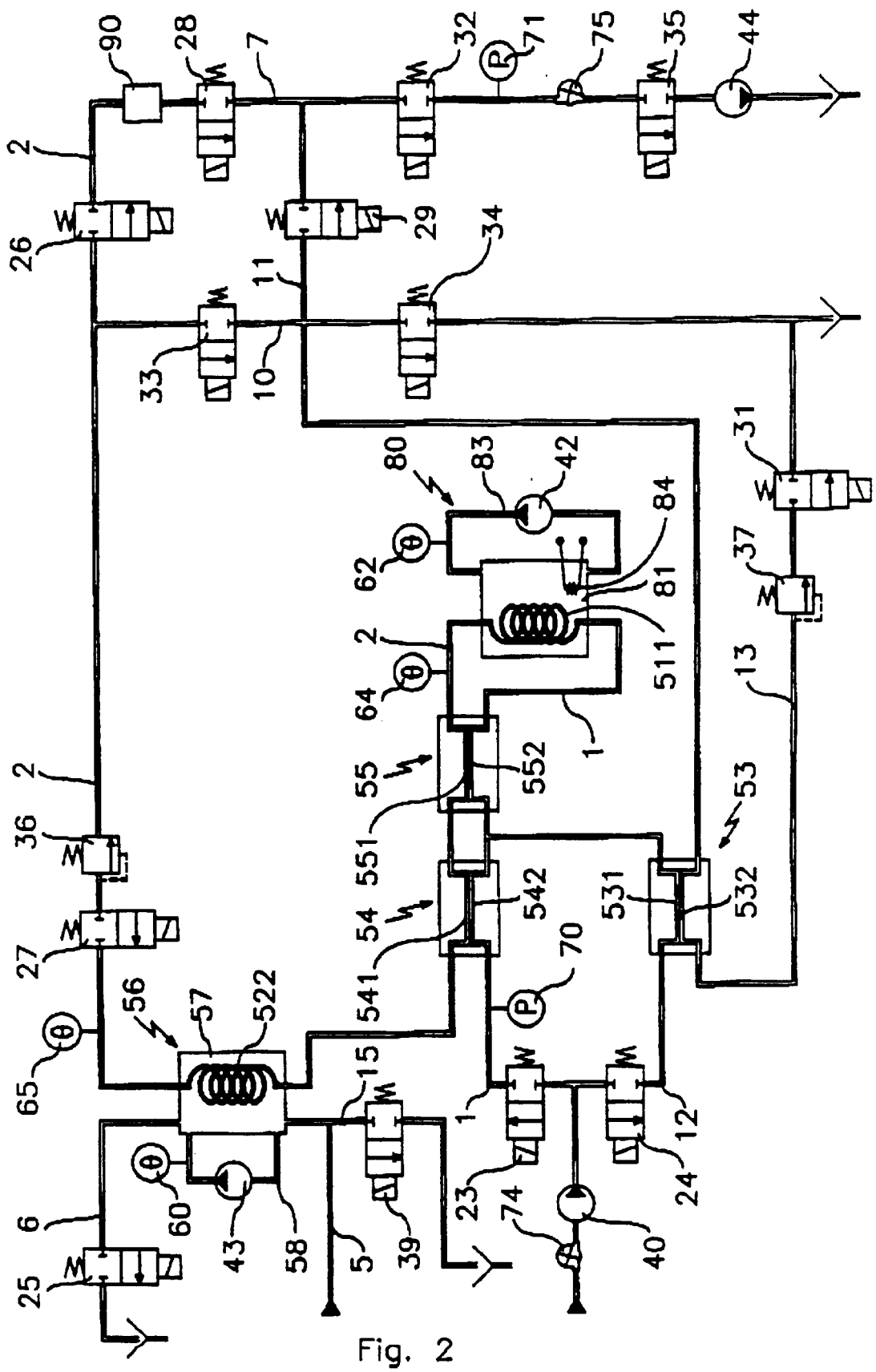
FIG. 2 represents the scheme of a second embodiment of a device according to the invention.

FIG. 2 represents a second embodiment of the device according to the invention. This device essentially comprises main heating means 80 with a chamber 511 for heating the liquid, and a main circuit with a first pipe 1 connected to an inlet of the heating chamber 511 and a second pipe 2 connected to an outlet of the heating chamber 511.

The main heating means 80 comprise a reservoir 81 containing a heating liquid, such as oil or ethylene glycol. The heating chamber 511, which is coil-shaped, is arranged in the reservoir 81 so as to be immersed in the heating liquid. An adjustable heating member 84 allows the temperature of the heating liquid to be raised. The heating means 80 also comprise liquid homogenization means consisting of a pipe 83 connecting the lower part to the upper part of the reservoir 81, on which a pump 42 is provided.

The first pipe 1 has an inlet which can be connected either to a water source or to a source of medical liquid. The following members are connected to the first pipe 1, in order, starting from the inlet of the pipe 1; a flow meter 74; a first pump 40; a valve 23; a first and a second additional heating means 541, 551.

The second pipe 2 connects the outlet of the heating chamber 511 to an inlet of a sterilizable connector 90, which has a first outlet for dispensing the sterile liquid. The following members are connected to the second pipe 2, in order, starting from the main heating means 80: first additional cooling means 552, which are advantageously combined with the second additional heating means 551 to form a first heat exchanger 55; second additional cooling means 542, which are advantageously combined with the first additional heating means 541 to form a second heat exchanger 54; main cooling means 56; a valve 27; first pressure adjustment means 36, consisting of a valve tared to a first pressure threshold (five bar); and a valve 26.

Figure 4:
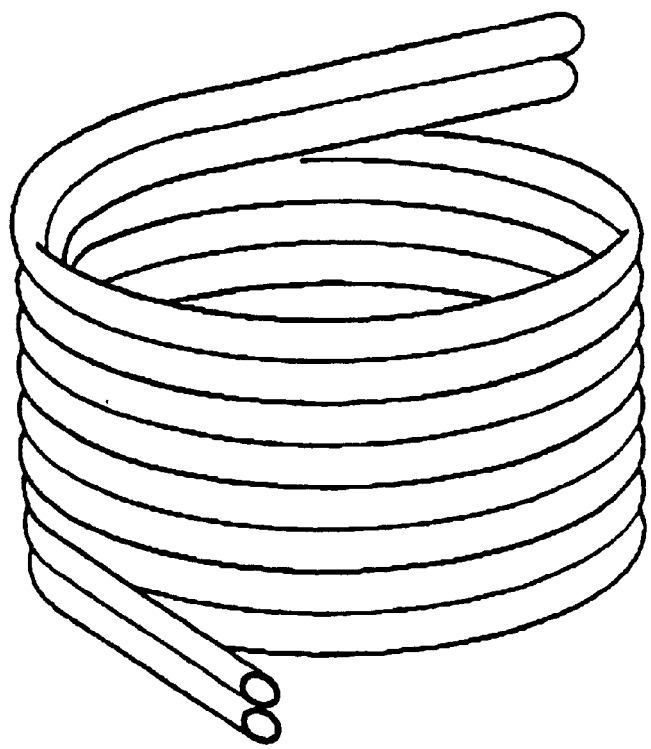
FIG. 4 is a view in perspective of a second embodiment of a heat exchanger according to the invention.

The heat exchangers 54, 55 are preferably shaped like the exchanger represented in FIG. 4, i.e. with the junction on a part of their length of the pipe 1 and of the pipe 2. The two portions of joined pipes are formed into twin helical coils, and both the inside and the outside of the cylinder thus formed are covered with a material which is a good heat conductor.

The main cooling means 56 comprise a reservoir 57 with an inlet connected to a cold water source via a pipe 5 and an outlet connected to the drain via a pipe 6 on which is provided a valve 25. A drain pipe 15 fitted with a valve 39 is connected to the pipe 5 so that the reservoir 57 drains under gravity when the supply of water to the pipe 5 is interrupted and the valves 25 and 39 are opened. The pipe 2 includes a coil-shaped portion 522, which is arranged in the reservoir 57 so as to be immersed in the cold water. The cooling means 56 are also fitted with liquid homogenization means consisting of a recirculation pipe 58 connecting the lower part to the upper part of the reservoir 57, on which is provided a pump 43. During functioning, the pump 43 is permanently running, and the temperature of the water leaving the cooling means 56, which is measured by a temperature sensor 65 connected to the pipe 2, is compared with a reference temperature: when the temperature of the water leaving the cooling means 56 exceeds the reference temperature, the valve 25 is opened until the temperature of the water leaving the cooling means has fallen below the reference temperature.

The sterilization device represented in FIG. 2 also comprises a first discharge pipe 7 which is connected to a second outlet of the connector 90, as well as a second discharge pipe 10 which is connected to the second pipe 2 of the main circuit.

The first discharge pipe 7 is used for draining a patient's peritoneal cavity, when the device according to the invention is used for treating a patient by peritoneal dialysis; it is also used, partially, during the sterilization of the second pipe and of the connector 90. The following members are connected to the first discharge pipe 7, in order, starting from the connector 90; a first valve 28; a second valve 32; a second flow meter 75; a third valve 35; and a pump 44.

The second discharge pipe 10 has one end connected to the second pipe 2 of the main circuit, between the tared valve 36 and the valve 26, and its other end is connected to the drain. The second discharge pipe 10, which is provided with a first valve 33 and a second valve 34, is used during a peritoneal dialysis treatment, outside of the steps for infusing the patient.

The first and the second discharge pipes 7, 10 are connected via a connecting pipe 11, one end of which is connected to the pipe 7, between the valves 28 and 32, and the other end of which is connected to the pipe 10, between the valves 33 and 34. A valve 29 is provided on this connecting pipe 11.

The device represented in FIG. 2 also comprises means used specifically for sterilizing the second pipe 2 of the main circuit and the connector 90, namely a third pipe 12 mounted in parallel to the first pipe 1, and a fourth pipe 13 mounted in parallel to the second discharge pipe 10.

One end of the third pipe 12 is connected to the first pipe 1, between the pump 40 and the valve 23, and its other end is connected to the first pipe 1, between the two heat exchangers 54, 55. A valve 24 and third additional heating means 532 are provided on this third pipe 12, in the direction of circulation of the liquid.

One end of the fourth pipe 13 is connected to the second discharge pipe 10, between the valves 33 and 34, and its other end is connected to the pipe 10 downstream of the valve 34. A third additional cooling means 531, a second pressure adjustment means consisting of a valve 37 tared to a second pressure threshold (three bar) and a valve 31 are connected to this fourth pipe 13, in the direction of circulation of the liquid. Advantageously, the third additional heating means 532 are combined with the third additional cooling means 531 to form a heat exchanger 53 shaped like the exchanger represented in FIG. 4.

Like the device in FIG. 1, the device represented in FIG. 2 also includes a plurality of pressure and temperature measuring means provided at various points on the main circuit (pipes 1 and 2), on the first discharge pipe 7, on the main heating means 80 and on the main cooling means 56. In particular, a pressure sensor is connected to the following pipes, at the following points:

on the first pipe 1, between the valve 23 and the second exchanger 54 (reference number 70);

on the first discharge pipe 7, between the valves 32 and 35 (reference number 71).

A temperature sensor is connected to the following pipes, at the following points:

on the first pipe 1, at the outlet of the heating chamber 511 for the main heating means 80 (reference number 64);

on the pipe 83 for recirculating the heating liquid (reference number 62);

on the pipe 58 for recirculating the cooling liquid (reference number 60);

on the second pipe 2, between the main cooling means 56 and the valve 36 tared to a first pressure threshold (reference number 65).

The device represented in FIG. 2 also includes a control and checking unit (not shown). This unit receives the data measured by the pressure sensors 70, 71, by the temperature sensors 60, 62, 64, 65 and by the flow meters 74 and 75. From these data, from operating parameters communicated by an operator, and from calculation algorithms and control programs stored in a memory, the control unit controls and checks the various operating phases of the device.

The functioning of this device is not fundamentally different from the functioning of the device represented in FIG. 1.

During the sterilization phase of the pipe 2 and of the connector 90, the main cooling means 56 are not switched on: the pump 43 is stopped, the valves 25 and 39 are open, and the supply of water to the pipe 5 is interrupted so that the reservoir 57 is empty. The valves 24, 26, 27, 28, 29, 31 are open and the valves 23, 32, 33, 34, 35 are closed. When the circuit including the pipe 2 and of the connector 90 has been sterilized, the section of pipe 10 between its junction with pipe 2 and its junction with pipe 11 is sterilized in turn, by opening valve 33 and closing one of the valves 26, 28, 29. For example, the pressure in the main circuit between the pump 40 and the valve 36 tared to the first pressure value is five bar, the pressure between the valve 36 and the valve 37 tared to the second pressure value is three bar and the pressure downstream of the valve 37 is one bar (atmospheric pressure). The temperature of the heating liquid is adjusted such that, with suitable heat exchanger designs, and at an appropriate flowrate, the temperature of the water in line 12 downstream of the third exchanger 53 is 110° C., the temperature of the water at the outlet of the heating chamber 511 is 150° C., the temperature of the water downstream of the first and second exchangers 54, 55 and upstream of the third exchanger 53 is 130° C., and the temperature of the water in line 13 downstream of the third exchanger 53 is 60° C. The period for which the second pipe 2 and the connector 90 are left in contact with sterile water at 130° C. is sufficient to ensure their sterility, that is to say also that the sterilizing value F0 for the sterilization treatment applied to them is greater than the second threshold value F0min2.

During the standby phase in which the device is kept sterile, the valves 23, 27, 33, 34 are open and the valves 24, 26, 28, 29, 31, 32, 33, 35 are closed. The main cooling means 56 are switched on (pump 43 running, valve 39 closed, valve 25 intermittently open).

During the phase of infusing liquid, the valves 23, 26, 27, 28, 32 are open and all of the other valves are closed. The main cooling means 56 are switched on (pump 43 running, valve 25 intermittently open).

For example, during these last two phase, the pressure in the main circuit between the pump 40 and the valve 36 tared to the first pressure value is five bar and the pressure downstream of the valve 36 is one bar (atmospheric pressure). The temperature of the heating liquid is adjusted such that, with suitable heat exchanger designs, the temperature of the water at the outlet of the heating chamber 511 is 150° C., the temperature of the water downstream of the first and second exchangers 54, 55 is 60° C., and the temperature of the water downstream of the main cooling means is 37° C. For liquid flow rates less than or equal to about 300 ml/min., the operating conditions which have just been mentioned make it possible to ensure that the water or the medical liquid produced by the device is sterile. In other words, the sterilizing value F0 for the sterilization treatment applied to the water or to the medical liquid is greater than the first threshold value F0min1.

The invention is not limited to the embodiments which have just been described and is capable of variation.

What is claimed is:

1. A device for preparing a sterile liquid, comprising:
   main adjustable heating means for raising the temperature of a liquid inside a heating chamber;
   a main circuit comprising
      a first flow path comprising one end intended to be connected to a source of liquid to be sterilized and another end intended to be connected to an inlet of the heating chamber, and
      a second flow path comprising one end intended to be connected to an outlet of the heating chamber and another end intended to be connected to a connector comprising an outlet for delivering a sterile liquid;
   pumping means for circulating the liquid in the main circuit; and
   means for validating a sterilization treatment applied to the liquid, the means for validating comprising
      calculation means for calculating, from at least one operating parameter of the device, a parameter representing a sterilizing value for the sterilization treatment, and
      comparison means for comparing the calculated parameter to a threshold value corresponding to the sterility of the liquid.

2. The device according to claim 1, wherein the device further comprises control means for controlling at least one of the pumping means and the main adjustable heating means such that the calculated parameter is greater than the threshold value.

3. The device according to claim 1, wherein the calculation means calculates the calculated parameter from a mathematical model of the temperature distribution in the heating chamber, the temperature of the liquid entering or leaving the heating chamber, the temperature of heating liquid, and the flow rate of the liquid in the heating chamber.

4. The device according to claim 3, wherein the calculated parameter is a sterilizing value F0 defined by:

$$F0 = \int_0^L \frac{S}{Q} \times 10^{[\frac{T(y)-121}{10}]} dy$$

where
   L is the length of the heating chamber;
   S is the cross section of the heating chamber;
   Q is the flow rate of the liquid in the heating chamber; and
   T(y) is an equation representing the temperature distribution in the heating chamber.

5. The device according to claim 1, wherein the device further comprises means for preventing the formation of bubbles in the liquid during the sterilization of the liquid.

6. The device according to claim 5, wherein the means for preventing the formation of bubbles in the liquid comprises
   liquid pressure adjustment means, associated with the second flow path of the main circuit, for adjusting the pressure of the liquid to a pressure value above the vaporization pressure of the liquid irrespective of the temperature of the liquid.

7. The device according to claim 1, wherein the device further comprises a discharge flow path for connecting a second outlet of the connector to a drain.

8. The device according to claim 6, wherein the device further comprises a discharge flow path connected to the second flow path of the main circuit between the liquid pressure adjustment means and the connector.

9. The device according to claim 1, wherein the device further comprises additional liquid heating means associated with the first flow path of the main circuit.

10. The device according to claim 6, wherein the device further comprises main liquid cooling means associated with the second flow path of the main circuit upstream of the liquid pressure adjustment means.

11. The device according to claim 10, wherein the device further comprises additional liquid cooling means associated with the second flow path of the main circuit upstream of the main liquid cooling means.

12. The device according to claim 1, wherein the device further comprises means for sterilizing the second flow path and the connector.

13. The device according to claim 12, wherein the means for sterilizing the second flow path and the connector comprises additional liquid heating means associated with a parallel flow path parallel to the first flow path.

14. The device according to claim 9, wherein the additional liquid heating means is a first additional liquid heating means comprising two components, wherein the device further comprises a second additional liquid heating means associated with a parallel flow path parallel to the first flow path,
   wherein an upstream end of the parallel flow path is connected to the first flow path between the two components.

15. The device according to claim 12, wherein the means for sterilizing comprises means for preventing the formation of bubbles in the liquid during the sterilization of the second flow path and the connector.

16. The device according to claim 15, wherein the means for preventing the formation of bubbles in the liquid comprises liquid pressure adjustment means, associated with a discharge flow path, for adjusting the pressure of the liquid to at least a pressure value above the vaporization pressure of the liquid irrespective of the temperature of the liquid.

17. The device according to claim 12, wherein the means for sterilizing comprises means for validating a sterilization treatment applied to the second flow path and to the connector.

18. The device according to claim 17, wherein the validation means comprises
   calculation means for calculating, from a minimum value of the temperature of the liquid measured during a determined period of time at a point on a first discharge flow path, an additional parameter representing the sterilizing value for the sterilization treatment, and
   means for comparing the calculated additional parameter to a second threshold value corresponding to the sterility of the second flow path and the connector.

19. The device according to claim 18, wherein the device further comprises control means for controlling at least one of the pumping means and the main adjustable heating means such that the calculated additional parameter is greater than the second threshold value.

20. The device according to claim 18, wherein the additional parameter is a sterilizing value F02 defined by:

$$F02 = t \times 10^{[\frac{T-121}{10}]}$$

where
   T=minimum value of the temperature of the liquid, and
   t=period of time during which the minimum value T of the temperature of the liquid is measured.

21. The device according to claim 6, wherein the liquid pressure adjustment means is a first liquid pressure adjustment means comprising a first valve having variable opening, wherein the device further comprises a second liquid pressure adjustment means comprising a second valve having variable opening, and wherein the device further comprises control means for controlling gradual partial closure of the first valve and gradual complete opening of the second valve after sterilizing a portion of the device.

22. The device according to claim 7, wherein the device further comprises second pumping means associated with the discharge flow path.

23. The device according to claim 22, wherein the device further comprises control means designed such that the control means, at an initial stage of an operating phase of the device, controls the first pumping means so that the flow rate of the liquid in the main circuit is substantially constant, and the second pumping means so that the flow rate of liquid in the first discharge flow path gradually decreases, such that the flow rate of liquid flowing through the outlet of the connector gradually increases.

24. The device according to claim 1, wherein the main adjustable heating means for raising the temperature of a liquid inside the heating chamber comprises a container for containing a heating liquid in which the heating chamber is immersed, and means for heating the heating liquid.

25. The device according to claim 24, wherein the main adjustable heating means further comprises means for maintaining the temperature of the heating liquid substantially constant along the heating chamber.

26. The device according to claim 24, wherein the heating chamber comprises a pipe and the container for the heating liquid is another pipe concentric to the heating chamber.

27. A process for sterilizing a liquid using a device comprising main adjustable heating means for raising the temperature of a liquid inside a heating chamber, and a main circuit comprising a first flow path comprising one end intended to be connected to a source of liquid to be sterilized and another end intended to be connected to an inlet of the heating chamber, and a second flow path comprising one end intended to be connected to an outlet of the heating chamber and another end intended to be connected to a connector comprising an outlet for delivering a sterile liquid, wherein the process comprises:

heating the liquid in the heating chamber to a temperature and for a period suitable for sterilizing the liquid; and validating the sterilization treatment applied to the liquid by calculating, from at least one operating parameter of the device, a parameter representing the sterilizing value for the sterilization treatment and by comparing the calculated parameter to a threshold value corresponding to the sterility of the liquid.

28. The process according to claim 27, wherein the process further comprises controlling at least one of the pumping means and the main adjustable heating means so that the calculated parameter is greater than the threshold value.

29. The process according to claim 27, wherein the process further comprises calculating the calculated parameter from a mathematical model of the temperature distribution in the heating chamber, the temperature of the liquid entering or leaving the heating chamber, the temperature of the heating liquid, and the flow rate of the liquid in the heating chamber.

30. The process according to claim 29, wherein the calculated parameter is a sterilizing value F0 defined by:

$$F0 = \int_0^L \frac{S}{Q} \times 10^{[\frac{T(y)-121}{10}]} dy$$

where

L is the length of the heating chamber;

S is the cross section of the heating chamber;

Q is the flow rate of the liquid in the heating chamber; and

T(y) is an equation representing the temperature distribution in the heating chamber.

31. The process according to claim 27, wherein the process further comprises preventing the formation of bubbles in the liquid during the sterilization of the liquid.

32. The process according to claim 31, wherein the process further comprises pressurizing a part of the main circuit connected to the heating chamber such that, irrespective of the temperature of the liquid, the pressure of the liquid is greater than the vaporization pressure of the liquid.

33. The process according to claim 27, wherein the process further comprises sterilizing the second flow path and the connector by bringing the second flow path and the connector in contact with a sterile liquid at a temperature and for a period suitable for sterilizing the second flow path and the connector.

34. The process according to claim 33, wherein the process further comprises preventing the formation of bubbles in the liquid during the sterilization of the second flow path and the connector.

35. The process according to claim 34, wherein the process further comprises pressurizing at least the second flow path, the connector, and a part of a discharge flow path such that, irrespective of the temperature of the liquid, the pressure of the liquid is greater than the vaporization pressure of the liquid.

36. The process according to claim 33, wherein the process further comprises validating the sterilization treatment applied to the second flow path and the connector.

37. The process according to claim 36, wherein the validating comprises calculating, from a minimum value of the temperature of the liquid measured during a determined period of time at a point on a discharge flow path, an additional parameter representing the sterilizing value for the sterilization treatment, and comparing the calculated additional parameter to a second threshold value corresponding to the sterility of the second flow path and the connector.

38. The process according to claim 37, wherein the process further comprises controlling at least one of the pumping means and the main adjustable heating means so that the calculated additional parameter is greater than the second threshold value.

39. The process according to claim 38, wherein the additional parameter is a sterilizing value F02 defined by:

$$F02 = t \times 10^{[\frac{T-121}{10}]}$$

where

T=minimum value of the temperature of the liquid, and t=period of time during which the minimum value T of the temperature of the liquid is measured.

40. The process according to claim 32, wherein the process further comprises pressurizing the part of the main circuit connected to the main adjustable heating means by using a first valve having variable opening, and pressurizing at least the second flow path, the connector, and a part of a discharge flow path by using a second valve having variable opening.

41. The process according to claim 40, wherein the process further comprises controlling, after sterilizing a portion of the device, the gradual partial closure of the first valve and the gradual complete opening of the second valve.

42. The process according to claim 27, wherein the process further comprises, at an initial stage of a phase of producing sterile liquid, causing a flow of the liquid in the main circuit at a substantially constant flow rate, and causing a flow of liquid in a discharge flow path at a gradually decreasing flow rate, such that the flow rate of liquid available at the outlet of the connector gradually increases.

43. The process according to claim 27, wherein the flow rate of the liquid to be sterilized is chosen so that the flow of the liquid is turbulent in the heating chamber.

44. The device of claim 1, wherein the at least one operating parameter of the device comprises at least one of the flow rate of the liquid in the heating chamber, the temperature of the liquid entering the heating chamber, the temperature of the liquid leaving the heating chamber, the temperature of heating liquid entering the main adjustable heating means, and the temperature of heating liquid leaving the main adjustable heating means.

45. The process according to claim 27, wherein the at least one operating parameter of the device comprises at least one of the flow rate of the liquid in the heating chamber, the temperature of the liquid entering the heating chamber, the temperature of the liquid leaving the heating chamber, the temperature of heating liquid entering the main adjustable heating means, and the temperature of heating liquid leaving the main adjustable heating means.

46. The process according to claim 27, wherein the device used in the process further comprises a discharge flow path associated with a second outlet of the connector.

* * * * *